US005557022A

United States Patent [19]

Murata et al.

[11] Patent Number: 5,557,022
[45] Date of Patent: Sep. 17, 1996

[54] AROMATIZATION PROCESS

[75] Inventors: Kazuhisa Murata; Hirobumi Ushijima, both of Tsukuba, Japan

[73] Assignee: Agency of Industrial Science And Technology, Japan

[21] Appl. No.: 323,810

[22] Filed: Oct. 17, 1994

[30] Foreign Application Priority Data

Dec. 7, 1993 [JP] Japan .................................. 5-340174

[51] Int. Cl.$^6$ ............................ C07C 15/00; C07C 5/367
[52] U.S. Cl. ............................................. 585/407; 585/430
[58] Field of Search .................................. 585/408, 409, 585/407, 430, 435, 446, 469, 477; 502/181, 185, 174

[56] References Cited

U.S. PATENT DOCUMENTS

| | | | |
|---|---|---|---|
| 4,066,712 | 1/1978 | Harris | 260/668 D |
| 4,116,880 | 9/1978 | Olah | 252/429 R |
| 4,122,040 | 10/1978 | McCarroll | 252/447 |
| 4,482,641 | 11/1984 | Wennerberg | 502/182 |

OTHER PUBLICATIONS

Kirk–Othmer Encyclopedia of Chemical Technology, vol. 4, p. 161 & p. 184.

*Primary Examiner*—Asok Pal
*Assistant Examiner*—Bekir L. Yildirim
*Attorney, Agent, or Firm*—Lorusso & Loud

[57] ABSTRACT

A non-aromatic organic compound is converted into aromatic hydrocarbons by a process in which the non-aromatic organic compound is contacted with a diamond-like carbonaceous catalyst at a temperature of 200°–1,500° C. The catalyst is a carbonaceous material which does not show any peak at 2θ of about 25° attributed to C(002) diffraction in a powder X-ray diffraction pattern thereof or which shows a peak at 2θ of about 25° attributed to C(002) diffraction in a powder X-ray diffraction pattern thereof and has a C(002) interplanar spacing greater than 0.3440 nm.

4 Claims, No Drawings

AROMATIZATION PROCESS

BACKGROUND OF THE INVENTION

1. Field of the Invention

This invention relates to a process for the production of aromatics from a non-aromatic organic compound.

2. Description of Prior Art

Conversion of a natural gas into aromatic hydrocarbons is one of the important techniques for the effective utilization of resources. Various methods have been hitherto proposed for the conversion of methane into aromatics. These methods include as follows:

(1) Dehydrogenation-oligomeration:

Calculation of thermodynamics reveals that methane is converted to benzene at above 1400K. Since carbon is produced at above 800K, this method is not practically promising (Amenomiya et al, Catal. Rev.-Sci. Eng., 32 (3), 163–227 (1990));

(2) Catalytic conversion:

Methane is catalytically converted into benzene using Mo-H-ZSM5. This method has a problem because the yield is extremely low.

(3) Oxidative coupling:

Methane is converted into benzene using H-ZSM5 as a catalyst and nitrous oxide as an oxidation agent (Anderson et al, Appl. Catal., 19, 141–152 (1985)). Methane is converted into benzene by oxidation using $K/BaCO_3$ as a catalyst (Claridge et al, Appl. Catal., A 89, 103 (1992)). Methane is first converted by oxidative coupling into ethane and/or ethylene which, in turn, are polymerized into benzene using H-ZSM5 as catalyst (otsuka et al, Chem. Lett. 1995–1958 (1986)). These method has a problem because it is necessary to perform the reaction with a low methane conversion since otherwise a large amount of carbon and carbon dioxide would be produced and because the yield of benzene is very low.

(4) Pyrolysis on carbon fibers:

Methane is pyrolyzed on carbon fibers. Produced are $C_2$ hydrocarbons rather than aromatics.

SUMMARY OF THE INVENTION

It is, therefore, the prime object of the present invention to provide a simple, one-stage process which can yield aromatics from non-aromatic organic compounds with a high yield.

In accomplishing the above object, the present invention provides a process for the conversion of a non-aromatic organic compound into aromatics, comprising contacting the non-aromatic organic compound with a diamond-like carbonaceous material at a temperature of 200°–1,500° C.

The term "diamond-like carbonaceous material" used in the present specification is intended to refer to (a) a cabonaceous material which does not show any peak at $2\theta$ of about 25° attributed to C(002) diffraction in a powder X-ray diffraction pattern thereof, namely diamond, and (b) a carbonaceous material which shows a peak at $2\theta$ of about 25° attributed to C(002) diffraction in a powder X-ray diffraction pattern thereof and which has a C(002) interplanar spacing of not smaller than 0.3440 nm.

Thus, the carbonaceous material used as a catalyst in the present invention is typically diamond. From the standpoint of economy, the use of diamond is not advantageous. A carbonaceous material having a structure similar to diamond and obtained by thermally decomposing an organic substance in vacuum or in an inert atmosphere at a temperature of 500°–2,000° C. may be used as the diamond-like substance as long as it shows the above-specified C(002) interplanar spacing in a powder X-ray diffraction pattern thereof. Graphite shows a peak at $2\theta$ of about 25° attributed to C(002) diffraction in a powder X-ray diffraction pattern thereof but has a C(002) interplanar spacing of less than 0.3440 nm. Therefore, graphite is excluded from the scope of the diamond-like carbonaceous material.

Other objects, features and advantages of the present invention will become apparent from the detailed description of the preferred embodiments to follow.

DETAILED DESCRIPTION OF THE PREFERRED EMBODIMENTS OF THE INVENTION

In the process according to the present invention, a non-aromatic compound is contacted with a diamond-like carbonaceous material at an elevated temperature so that the compound is converted into aromatics. Any non-aromatic organic compound may be used as a raw material for the production of aromatics. Illustrative of suitable non-aromatic organic compounds are aliphatic hydrocarbons such as methane, ethane, ethylene and propane; alicyclic hydrocarbons such as cyclohexane; amines such as methylamine, ethylamine, diethylamine, triethylamine, n-butylamine, ethylenediamine and propyldiamine; alcohols such as ethanol, propanol, cyclohexanol, cyclododecanol and adamantanol; ketones such as acetone, methyl isobutyl ketone and cyclohexanone; aldehydes such as acetaldehyde and propionaldehyde; esters such as ethyl acetate and γ-butylolactone; ethers such as ethyl ether, methyl vinyl ether, tetrahydrofuran and dioxane; carboxylic acids such as acetic acid, butyric acid and oxalic acid; and sulfur compounds such as ethyl sulfide, propyl sulfide, thioglycol, 1,2-propanedithiol, dipropyl sulfide and dipropyl disulfide. These organic compounds may be used singly or in combination of two or more.

The aromatization of the non-aromatic organic compound may be performed in a batch system or in a continuous flow system. When the aromatization is performed in a continuous flow system, it is preferred that the non-aromatic compound be previously mixed with a carrier gas such as ammonia, nitrogen, carbon dioxide, carbon monoxide or a rare gas and that the mixed feed be contacted with the carbonaceous material. When the non-aromatic compound is a liquid at room temperature, the mixing with the carrier gas is performed after vaporization of the compound.

The conversion of the non-aromatic organic compound into aromatics is generally performed at a temperature of 200°–1,500° C., preferably 400°–1,200° C. The kind of the aromatics thus produced varies depending upon the kind of the non-aromatic organic compound and the aromatization conditions. Examples of the aromatics include benzene, toluene, xylene, naphthalene, anthracene, pyridine, quinoline, thiophene, dibenzothiophene, furan and dibenzofuran.

The diamond-like carbonaceous material is preferably a product obtained by thermally decomposing an organic substance in vaccum or in an inert atmosphere at a temperature of 500°–2,000° C. The diamond-like carbonaceous material is preferably in the form of a powder.

Any organic substance may be used as a precursor of the carbonaceous material. Examples of organic substances include (a) relatively low molecular weight substances such as hydrocarbons, halogenated hydrocarbons, nitrogen-containing organic compounds, oxygen-containing organic compounds, phosphorus-containing organic compounds, sulfur-containing organic compounds, boron-containing organic compounds and selenium-containing organic compounds and (b) polymeric substances such as polymers or copolymers of aromatic compounds, polymers or copolymers of α,β-unsaturated compounds, natural polymers, polyesters, polyamindes, polyimides, phenol-formaldehyde resins, urea resins and melamine resins.

Illustrative of suitable hydrocarbons and halogenated hydrocarbons are pentane, octane, dodecane, dimethylpropane, dimethylbutane, cyclohexane, cyclododecane, adamantane, norbornane, benzene, toluene, naphthalene, chloropropyl and chlorocyclohexane.

Illustrative of suitable nitrogen-containing organic compounds are aliphatic amines such as ethylamine, diethylamine, triethylamine, n-butylamine, ethylenediamine and propanediamine; aromatic amines such as aniline and methylaniline; and heterocyclic compounds such as pyridine, quinoline, carbazole, 1,4,8,11-tetraazaundecane, 1,5,8,12-tetraazadodecane, 1,5,9,13-tetraazatridecane, 1,4,8,11-tetraazacyclotetradecane and 1,4,8,12-tetraazacyclopentadecane.

Illustrative of suitable oxygen-containing organic compounds are aliphatic alcohols such as ethanol and propanol; alicyclic alcohols such as cyclohexanol, cyclododecanol and adamantanol; aromatic alcohols such as phenol and bisphenol; ketones; aldehydes; esters; ethers and carboxylic acids.

Illustrative of suitable phosphorus-containing organic compounds are phosphine and phosphine compounds having one or more substituents such as an alkyl group, a phenyl group, an alkoxy group, a hydroxyl group, a halogen group and an amino group, e.g. triethylphosphine, triphenylphosphine, triethoxyphosphine, trihydroxyethylphosphine, trichloromethylphosphine, triaminoethylphosphine and 1,2-bis(diphenylphosphino)ethane. The use of a phosphorous-containing organic compound as a raw material for the production of the diamond-like carbonaceous material is particularly preferred.

Illustrative of suitable sulfur-containing organic compounds are thiols, dithiols, dialkylsulfides and aromatic thiophenes, e.g. ethyl sulfide, propyl sulfide, thioglycol, 1,2-propanedithiol, dipropyl sulfide, dipropyl disulfide, thiophene and dibenzothiophene.

Illustrative of suitable boron-containing organic compounds are borane, triethylborane, tributylborane, tri-n-butyl borate and chlorodiethylborane.

Illustrative of suitable selenium-containing organic compounds are dimethyl selenide and diethyl selenide.

The above relatively low molecular weight substances (a) preferably have a molecular weight of 500 or less, more preferably 16–300.

Illustrative of suitable polymers of aromatic compounds are those of an aromatic aldehyde such as a hydroxybenzaldehyde, a hydroxyphthaladehyde or a hydroxynaphthoaldehyde.

Illustrative of suitable copolymers of aromatic compounds are those of an aromatic substance with an aromatic aldehyde. The aromatic substance may be, for example, phenol, naphthalene, anthracene, phenanthrene, pyrene, indol, carbazole, thiophene or a derivative or mixture thereof. The aromatic aldehyde to be copolymerized with the aromatic substance may be, for example, benzaldehyde, naphthaldehyde, anthracenaldehyde, pyrenaldehyde, or a derivative or mixture thereof.

Illustrative of suitable polymers and copolymers of α,β-unsaturated compounds are those of α,β-unsaturated nitriles, α,β-unsaturated alcohols, α,β-unsaturated carboxylic acids, halogenated vinyl compounds, vinyl aromatics, vinyl ethers, olefins or acetylene polymers. Typical examples of the α,β-unsaturated compounds include acrylonitrile, vinyl alcohol, methyl acrylate, butadiene, vinyl chloride, vinyl acetate, styrene, methyl vinyl ether, vinylpyrrolidone, vinylpyridine, ethylene and propylene.

Illustrative of suitable natural polymers are starch, chitin, cellulose, keratin, lignin, gelatin and casein.

The above polymeric substances (b) may be used in conjunction with an inorganic or an organometallic substances including carbon materials such as activated carbon, graphite and mesophase pitch; silicon materials such as silicon powder, silicon carbide, silicon nitride and silica; aluminum materials such as aluminum powder, aluminum carbide, aluminum nitride and alumina; boron materials such as boron carbide and boron nitride; titanium materials such as titanium powder and titania; organosilicon materials such as polymethylsilane, ethyl silicate, triethylsilane and triphenylsilane; and organoaluminum materials such as aluminum isopropoxide and triethylaluminum.

The above organic substance is heated in vaccum (generally 1–50,000 Pa, preferably 10–5,000 Pa) or in the atmosphere of an inert gas such as nitrogen or argon at a temperature of 500°–2,000° C., preferably 800°–1,300° C., so that the organic substance is thermally decomposed into a carbonaceous material. Whether or not the thus obtained carbonaceous material is usable for the purpose of the present invention may be determined from the powder X-ray diffraction pattern thereof.

The diamond-like carbonaceous material, which does not contain such heavy metals as contained in the conventional methane aromatization catalysts, is light in weight and is able to be completely burnt after use. Therefore, the aromatization process can be carried out in an advantageous manner.

The following examples will further illustrate the present invention.

Reference Example

Preparation of Carbonaceous Materials Nos. 1–11:

Cyclohexane (0.8 g) was charged in a quartz tube at one, left side end portion thereof. While maintaining the cylohexane at a liquid nitrogen temperature, the quartz tube was evacuated for 3 hours. Then, the other, right side portion of the quartz tube was located in an electric oven and heated to 950° C., with the left side portion being heated with a ribbon heater, so that the cyclohexane contained in the left side portion was rapidly introduced into the right side portion. Thus, the cyclohexane was pyrolyzed at 950° C. for 35 minutes. After completion of the pyrolysis, the quartz tube was evacuated at that temperature for 30 minutes and, thereafter, cooled to room temperature, thereby to obtain a carbonaceous material No. 1 which deposited on the interior surface of the quartz tube. The yield was 0.126 g (15.8 %). The carbonaceous material was measured for magnetization at 25° C. at 5 kG to give the result shown in Table 1. The carbonaceous material was also subjected to powder X-ray diffraction pattern analysis. The interplanar distance $d_{002}$ and the thickness Lc of crystal stacks were determined from the diffraction at 2θ of about 25° (attributed to carbon (002) diffraction) and the diameter La of crystal stacks was determined from the diffraction at 2θ of about 42° (attributed to carbon (101) diffraction). The results are also shown in Table 1.

The above procedure was repeated in the same manner as described except that the pyrolysis temperature was increased to 1,000° C., 1,050° C. and 1,100° C. to give carbonaceous materials Nos. 2–4, respectively. The yields and properties of these materials are shown in Table 1.

The above procedure for the preparation of carbonaceous material No. 1 was repeated in the same manner as described except that the pyrolysis temperature was increased to 1,050° C. and that cyclohexane was replaced by di-n-propylamine, tri-n-propylphosphine, triphenylphosphine, dipropylsulfide, triethylborane (1M) diluted with hexane and dimethyl selenide to give carbonaceous materials Nos. 5–10, respectively, with the yields shown in Table 1. These materials had the properties summarized in Table 1.

Into a flask were charged 0.1 mol of pyrene, 0.125 mol of benzaldehyde, 3.3 g of activated carbon and 5 % by weight of p-toluenesulfonic acid catalyst. The mixture was reacted at 160° C. for 10 hours in an argon gas stream to obtain a condensed polynuclear aromatic hydrocarbon (COPNA resin). The COPNA resin (4 g) was then pyrolyzed at 1,000° C. for 24 hours in the atmosphere of argon to obtain a carbonaceous material No. 11. The yield and properties of this material are shown in Table 1.

and 2.0%, respectively. The methane conversion (C), selectivity (S) to benzene based on methane, yield of benzene (Y) based on methane and carbon yield (Z) are defined as follows:

$$C (\%) = \frac{W - W'}{W} \times 100$$

wherein W represents the amount of methane feed and W' represents the amount of unreacted methane.

$$S (\%) = \frac{B \times 6}{W - W'} \times 100$$

wherein B represents the amount of benzene produced and W and W' are as defined above.

$Y(\%) = C \times S/100$ $Z(\%) = 100 - (S + S1 + S2 + S3)$ wherein S1, S2 and S3 represent selectivities to ethane, ethylene and $C_3$ hydrocarbons, respectively, which were calculated in the same manner as the calculation of the selectivity to benzene.

TABLE 1

| Carbonaceous Material No. | Raw Material | Pyrolysis Temperature (°C.) | Yield (%) | Magnetization (emuG/g) | Spacing $d_{002}$ (nm) | Diameter La (nm) | Thickness Lc (nm) |
| --- | --- | --- | --- | --- | --- | --- | --- |
| No. 1 | cyclohexane | 950 | 15.8 | 0.378 | 0.347 | 2.056 | 1.732 |
| No. 2 | cyclohexane | 1,000 | 17.6 | 0.312 | 0.3508 | 2.363 | 1.50 |
| No. 3 | cyclohexane | 1,050 | 37.1 | 0.198 | 0.35 | 2.623 | 1.407 |
| No. 4 | cyclohexane | 1,100 | 36.8 | 0.0783 | 0.3527 | 1.971 | 1.80 |
| No. 5 | di-n-propylamine | 1,050 | 7.4 | 0.367 | 0.352 | 1.817 | 1.500 |
| No. 6 | tri-n-propylphosphine | 1,050 | 26.5 | 0.0167 | — | 1.573 | — |
| No. 7 | triphenylphosphine | 1,050 | 42.3 | 0.0239 | 0.361 | 1.968 | 1.728 |
| No. 8 | dipropylsulfide | 1,050 | 10.5 | 0.337 | 0.353 | 2.145 | 2.249 |
| No. 9 | triethylborane | 1,050 | 9.8 | 0.323 | 0.352 | 3.939 | 1.869 |
| No. 10 | dimethyl selenide | 1,050 | 15.4 | 0.433 | — | 1.686 | — |
| No. 11 | COPNA resin | 1,000 | 35.5 | 0.580 | 0.358 | — | 1.28 |

Conversion of Methane into Aromatics:

EXAMPLE 1

Carbonaceous material No. 3 (0.05 g) was packed in a quartz reaction tube together with 2 g of quartz sand. The reaction tube was heated to 1,100° C. at a rate of 8° C./minute, maintained at that temperature for 50 minutes and then cooled to room temperature, while continuously feeding a helium gas thereto at a rate of 45 ml/minute. Then, the helium gas feed was substituted by a feed of a mixed gas consisting of one volume of methane and 10 volume of helium. The mixed gas feed was passed through the packed layer of carbonaceous material No. 3 at a rate of 45 ml/minute while heating the reaction tube at a rate of 4° C./minute. After a temperature of 1,050° C. had been reached, the feeding of the mixed gas was further continued at that temperature. The gas discharged from the reaction tube 2 hours after a temperature of 1,050° C. had been reached was analyzed by gas chromatography to determine the methane conversion (C), selectivity (S) to benzene based on methane, yield of benzene (Y) based on methane and carbon yield (Z). The results were as summarized in Table 2. The gas chromatographic analysis also revealed that ethane, ethylene and a very small amount of $C_3$ hydrocarbons (propane and propylene) were produced. The selectivity to ethane and the yield of ethane were 22.9% and 7.1%, respectively. The selectivity and yield of ethylene were 6.5%

EXAMPLE 2

Example 1 was repeated in the same manner as described except that carbonaceous material No. 4 was used in lieu of carbonaceous material No. 1 and that the conversion reaction was performed at 1,100° C. The results are summarized in Table 2.

EXAMPLE 3

Example 1 was repeated in the same manner as described except that carbonaceous material No. 5 was used in lieu of carbonaceous material No. 1 and that the conversion reaction was performed at 1,100° C. The results are summarized in Table 2.

EXAMPLE 4–10

Example 1 was repeated in the same manner as described except that carbonaceous materials Nos. 5–11 were each used in lieu of carbonaceous material No. 1. The results are summarized in Table 2.

EXAMPLE 11

Example 1 was repeated in the same manner as described except that commercially available artificial diamond was used in lieu of carbonaceous material No. 1. The results are summarized in Table 2.

Comparative Example 1

Example 1 was repeated in the same manner as described except that commercially available graphite was used in lieu of carbonaceous material No. 1. The results are summarized in Table 2.

Comparative Example 2

Example 1 was repeated in the same manner as described except that carbonaceous material No. 1 was not charged into the reaction tube. Thus, the reaction tube contained quartz sand alone. The results are summarized in Table 2.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

TABLE 2

| Example No. | Carbonaceous Material | Reaction Temperature (°C.) | Methane Conversion (%) | Selectivity (%)/Yield (%) | | Carbon Yield (%) |
| --- | --- | --- | --- | --- | --- | --- |
| | | | | Benzene | $C_2$ (ethane, ethylene) | |
| 1 | No. 1 | 1,050 | 30.9 | 54.7/16.9 | 29.4/9.1 | 13.8 |
| 2 | No. 4 | 1,100 | 51.6 | 48.0/24.8 | 23.1/11.9 | 27.9 |
| 3 | No. 5 | 1,100 | 53.0 | 55.4/29.4 | 21.9/11.6 | 21.7 |
| 4 | No. 5 | 1,050 | 41.9 | 38.6/16.2 | 18.8/7.89 | 40.7 |
| 5 | No. 6 | 1,050 | 40.4 | 55.8/22.6 | 24.0/6.11 | 18.6 |
| 6 | No. 7 | 1,050 | 35.8 | 54.1/19.3 | 24.3/8.68 | 19.4 |
| 7 | No. 8 | 1,050 | 33.9 | 32.5/11.0 | 24.1/8.18 | 40.9 |
| 8 | No. 9 | 1,050 | 51.9 | 25.6/13.3 | 18.5/9.62 | 54.4 |
| 9 | No. 10 | 1,050 | 44.2 | 20.6/9.10 | 16.1/7.11 | 61.9 |
| 10 | No. 11 | 1,050 | 35.5 | 55.0/19.5 | 23.1/8.20 | 18.5 |
| 11 | diamond* | 1,050 | 36.9 | 56.1/20.7 | 25.2/9.28 | 15.9 |
| Comptv. 1 | graphite** | 1,050 | 26.3 | 10.7/2.81 | 23.2/6.1 | 63.1 |
| Comptv. 2 | quartz sand | 1,050 | 13.5 | 12.2/1.65 | 18.3/2.47 | 62.9 |

*No peak at 2θ of about 25° attributed to carbon (002) diffraction in a powder X-ray diffraction pattern
**$d_{002}$ interplanar spacing: 0.3376 nm

What is claimed is:

1. A process for the conversion of a non-aromatic organic compound into aromatics, comprising contacting the non-aromatic organic compound with a catalyst at a temperature of 200°–1,500° C., said catalyst being a carbonaceous material which shows a peak at 2θ of about 25° attributed to C(002) diffraction in a powder X-ray diffraction pattern thereof and which has a C(002) interplanar spacing greater than 0.3440 nm.

2. A process as claimed in claim 1, wherein said non-aromatic organic compound is a member selected from the group consisting of aliphatic hydrocarbons, alicyclic hydrocarbons and mixtures thereof.

3. A process as claimed in claim 1, wherein said second carbonaceous material is a product obtained by thermally decomposing an organic substance in vaccum or in an inert atmosphere at a temperature of 500°–2,000° C.

4. A process as claimed in claim 3, wherein said organic substance is at least one member selected from the group consisting of hydrocarbons, halogenated hydrocarbons, nitrogen-containing organic compounds, oxygen-containing organic compounds, phosphorus-containing organic compounds, sulfur-containing organic compounds, boron-containing organic compounds, selenium-containing compounds, polymers and copolymers of aromatic compounds, polymers and copolymers of α,β-unsaturated compounds, natural polymers, polyesters, polyamindes, polyimides, phenol-formaldehyde resins, urea resins and melamine resins.

* * * * *

UNITED STATES PATENT AND TRADEMARK OFFICE
CERTIFICATE OF CORRECTION

PATENT NO.  : 5,557,022
DATED       : September 17, 1996
INVENTOR(S) : MURATA et al It is certified that error appears in the above-indentified patent and that said Letters Patent is hereby corrected as shown below:

ON THE FACE OF THE PATENT:

Item
"[73] Assignee: Agency of Industrial Science And Technology" should read: --[73] Assignee: Director-General of Agency of Industrial Science And Technology--

Col. 1, line 33, "otsuka" should read --Otsuka--.

Signed and Sealed this

Seventeenth Day of June, 1997

Attest:

BRUCE LEHMAN

*Attesting Officer*

*Commissioner of Patents and Trademarks*